United States Patent [19]

Ohkawa et al.

[11] Patent Number: 5,552,552
[45] Date of Patent: Sep. 3, 1996

[54] CRYSTALLINE SALTS OF OPTICALLY ACTIVE AMINOCOUMARAN DERIVATIVES, THEIR PRODUCTION AND USE

[75] Inventors: Shigenori Ohkawa, Takatsuki; Shokyo Miki, Ikeda, both of Japan

[73] Assignee: Takeda Chemical Industries, Ltd., Osaka, Japan

[21] Appl. No.: 467,392

[22] Filed: Jun. 6, 1995

Related U.S. Application Data

[63] Continuation of Ser. No. 394,206, Feb. 24, 1995, abandoned, which is a continuation of Ser. No. 164,437, Dec. 9, 1993, abandoned.

[30] Foreign Application Priority Data

Dec. 9, 1992 [JP] Japan ..................... 4-329683

[51] Int. Cl.⁶ .................................................. C07D 405/06
[52] U.S. Cl. ........................................................ 546/196
[58] Field of Search ............................. 546/196; 514/320

[56] References Cited

U.S. PATENT DOCUMENTS

| | | | |
|---|---|---|---|
| 3,547,931 | 12/1970 | Kaiser et al. | 546/196 |
| 3,686,188 | 8/1972 | Heubner | 546/196 |
| 5,376,681 | 12/1994 | Aono et al. | 514/469 |

FOREIGN PATENT DOCUMENTS

| | | |
|---|---|---|
| 483772 | 5/1992 | European Pat. Off. . |
| 2054619 | 5/1992 | European Pat. Off. . |
| 2176782 | 1/1987 | United Kingdom . |

OTHER PUBLICATIONS

Karrer, *Organic Chemistry*, Third English Ed., Elsevier Pub. Co., Inc.: New York, pp. 101–103 (1947).

*Primary Examiner*—Brian M. Burn
*Attorney, Agent, or Firm*—Foley & Lardner

[57] ABSTRACT

A crystalline salt of an enantiomer of 5-amino-2,4,6,7-tetramethyl-2-(4-phenylpiperidinomethyl)-2,3-dihdrobenzo[b]furan which is stable and improved in solubility in water, is useful for an excellent lipidperoxide formation inhibitor.

3 Claims, 2 Drawing Sheets

CRYSTALLINE SALTS OF OPTICALLY ACTIVE AMINOCOUMARAN DERIVATIVES, THEIR PRODUCTION AND USE

This application is a continuation, of application Ser. No. 08/394,206, filed Feb. 24, 1995, (now abandoned) which is a continuation of Ser. No. 08/164,437, filed on Dec. 9, 1993 (now abandoned).

The present invention relates to a crystalline salt of optically active aminocoumaran derivative which is pharmaceutically effective particularly in improving, treating and preventing cerebral dysfunction associated with cerebral stroke or cranial trauma.

As lipidperoxide formation and related radical reaction in vivo were found to have various adverse effects on the living body via membrane disorder, enzyme disorder etc., there have been various attempts at pharmaceutical application of antioxidants and lipidperoxide formation inhibitors.

Major lipidperoxide formation inhibitors now in use in the pharmaceutical field are derivatives of natural antioxidants such as vitamin C, vitamin E and the like, and phenol derivatives [Kenji Fukuzawa, Japanese Journal of Clinical Medicine, Vol. 46, pp. 2269–2276 (1988)]. However, none are satisfactory for practical use because of weak action or side effects.

However, the present inventors have discovered an aminocoumaran derivative, represented by the following general formula (A), which excellently inhibits lipidperoxide formation, and have filed a patent application therefore (EP-A-0483772).

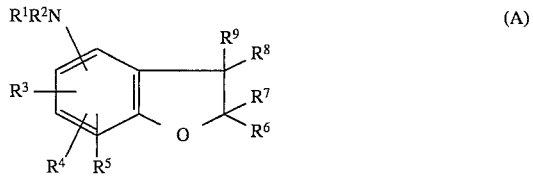

wherein $R^1$ and $R^2$ are the same or different and are a hydrogen atom, an acyl group, an alkoxycarbonyl group, an optionally substituted aliphatic or an optionally substituted aromatic group, $R^3$, $R^4$ and $R^5$ are the same or different and are an optionally acylated hydroxyl group, an optionally substituted amino group, an optionally substituted alkoxy group or an optionally substituted aliphatic group or two of $R^3$, $R^4$ and $R^5$ may be linked together to form an optionally substituted carbocyclic group; $R^6$ and $R^7$ are the same or different and are an optionally substituted aliphatic group, provided that at least on; of $R^6$ and $R^7$ has a methylene at the a-position; $R^8$ and $R^9$ are the same or different and are a hydrogen atom or an optionally substituted aliphatic group or an optionally substituted aromatic group, or a salt thereof.

Of the aminocoumaran derivatives represented by general formula (A), 5-amino-2,4,6,7-tetramethyl-2-(4-phenylpiperidonomethyl)-2,3-dihydrobenzo[b]furan, represented by formula (B)

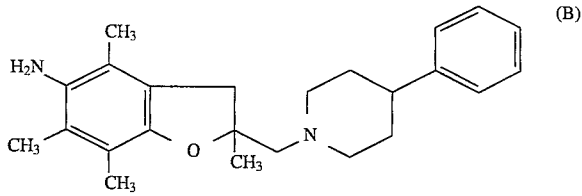

is described in the above publication as a sparingly water-soluble free form. Also, having asymmetric carbon atoms in its molecular structure, this derivative (B) occurs in two optical isomers, namely (R) and (S) configurations. Derivative (B) is described as a mixture (racemate) of these enantiomers in the above publication. However, it is not suitable for pharmaceutical preparations because it is hygroscopic and hence unstable. Also, there have been no injectable lipidperoxide formation inhibitors which are satisfactory from the viewpoint of action, water solubility, stability (storage stability) and other aspects. Accordingly, there is demand for the development of such agents.

The present inventors investigated means of solving the above problems. Specifically, the inventors attempted to separate optical isomers and form salts of 5-amino-2,4,6,7-tetramethyl-2-(4-phenylpiperidinomethyl)-2,3-dihydrobenzo[b]furan compound B, chosen from the above-described compounds represented by general formula (A), which are useful in improving, treating and preventing cerebral dysfunction associated with cerebral stroke or cranial trauma. Despite the generally accepted fact that any compound is difficult to crystallize for the first time, the inventors succeeded in creating a crystalline salt of an enantiomer of compound B, and unexpectedly found it stable and water-soluble and hence very useful for injectable preparations. The inventors conducted further investigation based on this finding, and developed the present invention.

Accordingly, the present invention provides a crystalline salt of an enantiomer of 5-amino-2,4,6,7-tetramethyl-2-(4-phenylpiperidinomethyl)-2,3-dihydrobenzo[b]furan, particularly the dihydrochloride and fumarate thereof, their production and lipidperoxide formation inhibitory preparation containing them.

Figure 1:
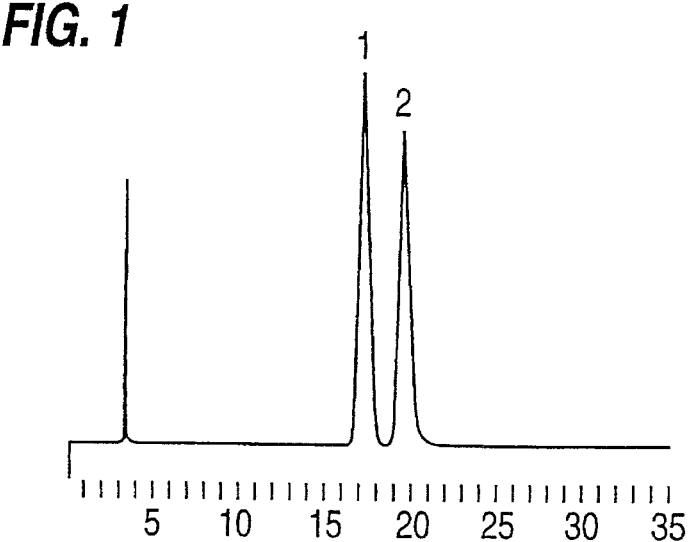
FIG. 1 shows the liquid chromatography results of the compound of Example 67 of EPA 483772.

The crystalline salt of the present invention is a crystalline salt of a compound (enantiomer) represented by the following formula (I) or (II):

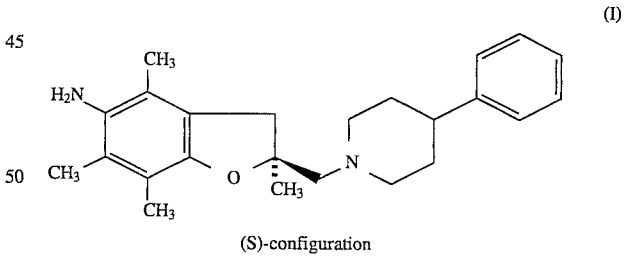

(S)-configuration

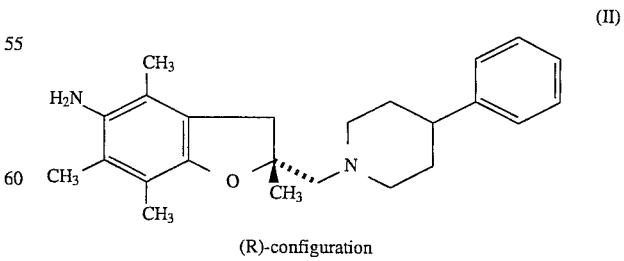

(R)-configuration

The crystalline salt of the present invention is a crystal of a salt of enantiomer (I) or (II) of 5-amino-2,4,6,7-tetramethyl-2-(4-phenylpiperidinomethyl)-2,3-dihydrobenzo[b]furan with a pharmacologically acceptable acid, e.g., an inorganic acid such as hydrochloric acid, hydrobromic acid, sulfuric acid or phosphoric acid, an organic acid such as acetic acid, fumaric acid, maleic acid, tartaric acid, mandelic acid, methanesulfonic acid, benzenesulfonic acid or toluenesulfonic acid, or an amino acid such as aspartic acid or glutamic acid.

The crystalline salt of the present invention may be mono- or di-salt of acid.

The crystalline salt of the present invention is preferably a dihydrochloride, fumarate or the like, more preferably dihydrochloride of (S)—(+) configuration or the like.

The crystalline salt of the present invention is produced by (1) reacting 5-amino-2,4,6,7-tetramethyl-2-(4-phenylpiperidinomethyl)-2,3-dihydrobenzo [b]furan (Compound B) with an optically active organic acid or (2) reacting an enantiomer of Compound B with an acid.

In the above-mentioned method (1), the crystalline salt of the present invention can be concretely produced by the following process (a) or (b)

(a) process for producing the crystalline salt which comprises mixing Compound B and an optically active organic acid in a solvent to yield a uniform solution.

(b) process for producing the crystalline salt which comprises condensing Compound B with an optically active organic acid to a diastereomeric mixture of amides, separating and purifying it, and then performing hydrolysis.

In process (a) or (b), typical optically active organic acids include organic carboxylic acids, organic phosphoric acids or organic sulfonic acids having an asymmetric center in the molecule. Preferable examples of optically active organic acids include substituted (−)—or (+)—tartaric acids such as (−)—or (+)—diacetyltartaric acid, (−)—or (+)—ditoluyltartaric acid, (−)—or (+)—dibenzoyltartaric acid, etc, (−)—or (+)—tartaric add, (−)—or (+)—malic acid, (−)—or (+)—mandelic acid, (−)—or (+)—lactic acid, (+)—camphor-10-sulfonic acid, (+)—3-bromocamphor-10-sulfonic acid, MTPA (α-methoxy-α-(trifluoromethyl)phenylacetic acid), menthoxyacetic acid, etc., especially (−)—or (+)—mandelic acid etc. in process (a) and MTPA, menthoxyacetic acid, etc. in process (b).

In process (a), solvents which can be used include water, alcohols (e.g., methanol, ethanol, propanol, isopropanol, butanol, ethers (e.g., ethyl ether, tetrahydrofuran, dioxane), esters (e.g., ethyl acetate, methyl acetate), ketones (e.g., acetone), nitriles (e.g., acetonitrile), amides (e.g., dimethylformamide, dimethylacetamide) and dimethylsulfoxide. These may be used singly or in combination. It is preferable to use a mixed solvent of methanol, acetonitrile, ethyl acetate, ether etc.

In process (a), it is common practice to use the optically active organic acid in a ratio of about 0.5 to 5 equivalents, preferably about 0.5 to 2 equivalents per equivalent of Compound B. Although the mount of solvent relative to that of Compound B varies depending on the kind of solvent, it is normally about 5 to 30 parts by weight per part by weight of Compound B in the case of methanol-acetonitrile solvent. This process (a) is carried out at 0° to 100° C., preferably 20° to 50° C. Upon mixture of Compound B and the optically active organic acid, a crystalline salt forms instantaneously.

In process (b), the diastreomeric mixture of amides can be produced by condensing Compound B with an optionally active organic acid according to a conventional method such as the acid chloride method, etc.

In process (b), the diastereomeric mixture of amides can be separated and purified by means of conventional separation and purification such as fractional crystallization or silica gel chromatography.

In process (b), the hydrolysis may be acidic hydrolysis (using an inorganic acid such as hydrochloric acid, sulfuric acid or phosphoric acid, an organic acid such as methanesulfonic acid, or an acidic ion exchange resin) or basic hydrolysis (using a base such as sodium hydroxide or potassium hydroxide, with water alone or with a combination of water and an organic solvent such as methanol or ethanol).

Additionally, if desired, to the crystalline salt-containing solution obtained in method (1) may be added an organic solvent, in which the salt is sparingly soluble (e.g., ether, hexane, ethyl acetate, etc.), in an amount (weight) about 1 to 50 times, preferably about 3 to 10 times, the mount of the solution; the mixture may be then kept standing at about 0° to 30° C. for about 0.5 to 24 hours, and the resulting precipitate (optically active organic acid salt) may be collected by filtration.

Also, the organic solvent in which the salt is sparingly soluble may be added after the crystalline salt-containing solution obtained in method (1) is concentrated (under reduced pressure or other conditions) at about 20° to 100° C. until its volume decreases to half to quarter of the original volume.

In method (2), an enantiomer of Compound B is reacted with an acid, for example, the above-described pharmacologically acceptable acid. Concretely, an enantiomer of Compound B is mixed with an acid in a solvent to yield a uniform solution.

The solvent for this method is the same as used in method (1). Temperature and time in this method are the same as for process (1).

Additionally, if desired, the desired product may be separated from the solution obtained in method (2), which contains the desired crystalline salt, in the same manner as for method (1).

The enantiomer of Compound B used as a starting material in method (2) can be produced by adding, an aqueous solution of an inorganic base such as an alkali metal carbonate, hydrogen carbonate or hydroxide such as potassium carbonate, sodium carbonate, sodium hydrogen carbonate, sodium hydroxide or potassium hydroxide to the optically active organic acid salt obtained in method (1) and separating by a means of separation such as filtration or solvent extraction. The amount of base used is about 1 to 10 parts by weight per part by weight of the salt.

Alternatively, the enantiomer of Compound B can be produced by subjecting Compound B or salt thereof (e.g., salt with the above-described pharmacologically acceptable acid) to chromatography using an enantiomer separation column (chiral column) such as ENANTIO-OVM (Tosoh Corporation) or the CHIRALCEL Series (Daisel Chemical Industries, Ltd.) and developing the chromatogram with one or more organic solvents such as water, various buffers (e.g., phosphate buffer), alcohols (e.g., methanol, ethanol), nitriles (e.g., acetonitrile), ethers (e.g., tetrahydrofuran) and hydrocarbons (e.g., hexane).

Compound B used as a starting material for the crystalline salt of the present invention is produced in accordance with the method described in Example 67 of EP-A-0483772.

The crystalline salt of the present invention improves the metabolism of higher unsaturated fatty acids (e.g., linolic acid, γ-linolenic acid, α-linolenic acid, arachidonic acid, di-homo-γ-linolenic acid, eicosapentaenic acid) and particularly exhibits circulatory system improving actions and antiallergic actions such as lipidperoxide formation inhibitory action (antioxidant action), 5-lipoxygenase system metabolite [e.g., leukotrienes, 5-hydroperoxyeicosatetraenic acid (HPETE), 5-hydroxyeicosatetraenic acid (HETE), lipoxins, leukotoxins] production suppressing action, thromboxane $A_2$ synthetase inhibitory action, prostaglandin $I_2$ synthetase retention promoting action, $LTD_4$ receptor antagonistic action and active oxygen species eliminating action.

Of these actions, the crystalline salt of the present invention exhibits marked lipidperoxide formation inhibitory action (antioxidant action).

The crystalline salt of the present invention is low in toxicity and prevalence of side effects.

The crystalline salt of the present invention is therefore therapeutically and prophylactically effective against thrombosis due to platelet agglutination, ischemic diseases due to arterial smooth muscle contraction or vasospasm in heart, lung, brain or kidney (e.g., myocardial infarction, cerebral stroke), nerve degeneration diseases (e.g., Parkinsonism, Alzheimer's disease, Lou Gehrig's disease, myodystrophy), functional disorders due to central nervous damages such as cranial trauma and spinal trauma, memory or emotional disorders (disorders associated with nervous cell necrosis etc. caused by oxygen deficiency, brain damage, cerebral stroke, cerebral infarction, cerebral thrombosis etc.), convulsions and epilepsies following cerebral stroke, cerebral infarction, cerebral surgery or cranial trauma, nephritis, pulmonary failure, bronchial asthma, inflammations, arteriosclerosis, atherosclerosis, hepatitis, acute hepatitis, liver cirrhosis, hypersensitive hepatitis, immunodeficiencies, circulatory diseases (myocardial infarction, cerebral stroke, cerebral edema, nephritis etc.) resulting from damage of enzyme, tissue, cell etc. caused by active oxygen species (e.g., superoxide, hydroxyl radical), tissue fibrosis, cancer and other diseases in mammals (e.g., mice, rats, rabbits, dogs, monkeys, humans), and is pharmaceutically useful as an antithrombotic agent, antivasospasmotic agent, antiasthmatic agent, antiallergic agent, cardiac/cerebral circulation improving agent, nephritis remedy, hepatitis remedy, tissue fibrosis inhibitor, active oxygen species eliminator, arachidonic cascade substance regulation improving agent and as other varieties of agent.

The crystalline salt of the present invention can be safely administered orally or non-orally, as such or in pharmaceutical compositions (e.g., tablets, capsules, liquids, injections, suppositories) along with pharmacologically acceptable carriers, excipients and other additives. The crystalline salt of the present invention, soluble in water, is advantageously administered as an injectable preparation. Although dose varies depending on subject, route of administration, symptoms and other factors, it is advantageous to administer it normally at about 0.01 mg/kg to 20 mg/kg body weight, preferably about 0.1 mg/kg to 10 mg/kg body weight, and more preferably about 0.5 mg/kg to 10 mg/kg body weight per dose once to three times daily, when non-orally administered to adult patients with circulatory disease.

The present invention is hereinafter described in more detail by means of the following working examples, analytical example and test example, which are not to be construed as limitative.

Example 1

(S)—(+)-5-amino-2,4,6,7-tetramethyl-2-(4-phenylpiperidinomethyl)-2,3-dihydrobenzo[b]furan (S)—(+)—mandelate To a solution of 35.4 g of (±)-5-amino-2,4,6,7-tetramethyl-2-(4-phenylpiperidinomethyl)-2,3 -dihydrobenzo[b] furan in 500 ml of chloroform was added a solution of 14.78 g of (S)—(+)—mandelic acid in 300 ml of methanol, followed by concentration. To the residue was added about 500 ml of ether; the resulting precipitate was collected by filtration and washed with ether. The resulting 35.4 g crude crystal was subjected to the following recrystallizing procedure. Specifically, the crude crystal was dissolved in methanol-acetonitrile (2:1) (1 liter). After the solution was concentrated to about 100 ml volume, about 500 ml of ether was added, and the mixture was kept standing at 20° C. The resulting precipitate was finely milled, then filtered and washed witch ether. The above procedure was repeated in two cycles (first yield 21.96 g) to yield 19.90 g of (S)—(+) -5-amino-2,4,6,7-tetramethyl-2-(4 -phenylpiperidinomethyl)-2,3-dihydrobenzo[b]furan (S)—(+)—mandelate.

Melting point: 186°–190° C.

$[\alpha]^{27}$ :+57.1° (c=1.230, methanol)

Elemental analysis (for $C_{24}H_{32}N_2O \cdot C_8H_8O_3$):

Calculated: C, 74.39; H, 7.80; N, 5.42

Found: C, 74.31; H, 7.83; N, 5.38

Example 2

(R)—(−)-5-amino-2,4,6,7-tetramethyl-2-(4-phenylpiperidinomethyl)-2,3-dihydrobenzo [b]furan (R)—(−)—mandelate The mother liquor of Example 1 was concentrated to dryness. The resulting 28.2 g residue was dispensed to 500 ml of ethyl acetate and 500 ml of a 0.5 N aqueous solution of sodium hydroxide. The organic layer was washed by sequential additions of a 0.5 N aqueous solution of sodium hydroxide, a saturated aqueous solution of sodium hydrogen carbonate and saturated saline and then dried over anhydrous sodium carbonate, followed by concentration to dryness. The resulting 20 g residue and 8.35 g of (R)—(−)—mandelic acid were treated in the same manner as in Example 1 to yield 20.41 g of (R)—(−)-5-amino-2,4,6,7-tetramethyl-2-(4-phenylpiperidinomethyl)-2,3-dihydrobenzo [b]furan (R)—(−)—mandelate.

Melting point: 186°–191° C.

$[\alpha]^{27}$ :−57.0° (c=1.090, methanol)

Elemental analysis (for $C_{24}H_{32}N_2O \cdot C_8H_8O_3$):

Calculated: C, 74.39; H, 7.80; N, 5.42

Found: C, 74.26; H, 7.78;N, 5.54

Example 3

(S)—(+)-5-amino-2,4,6,7-tetramethyl-2-(4-phenylpiperidinomethyl)-2,3-dihydrobenzo [b]furan dihydrochloride 19.8 g of (S)—(+)-5-amino-2,4,6,7-tetramethyl-2-(4-phenylpiperidino-methyl)-2,3-dihydrobenzo [b]furan (S)—(+)-mandelate was dispensed to 500 ml of ethyl acetate and 500 ml of a 0.5 N aqueous solution of sodium hydroxide. The organic layer was washed by sequential additions of a 0.5 N aqueous solution of sodium hydroxide, a saturated aqueous solution of sodium hydrogen carbonate and saturated saline and then dried over anhydrous sodium carbonate, followed by concentration to dryness. The resulting about 15 g residue was dissolved in 140 ml of methanol, and 23.3 ml of an ethyl acetate solution in 4 N hydrochloric acid, followed by concentration to dryness. The resulting residue was recrystallized from ethyl acetate to yield a crude crystal, which was again recrystallized from methanol-ethyl acetate to yield 13.84 g of (S)—(+)-5-amino-2,4,6,7-tetramethyl-2-(4-phenylpiperidinomethyl)-2,3-dihydrobenzo [b]furan dihydrochloride.

Melting point: 226° C. (decomposed)

$[\alpha]^{26}$ :+27.820 (c=1.054, methanol)

Elemental analysis (for $C_{24}H_{32}N_2O \cdot H_2Cl_2$):

Calculated: C, 65.90; H, 7.83; N, 6.40; Cl, 16.21

Found : C, 65.60; H, 7.89; N, 6.37; Cl, 16.01

Example 4

(R)—(–)-5-amino-2,4,6,7-tetramethyl-2-(4-phenylpiperidinomethyl)-2,3-dihydrobenzo [b]furan dihydrochloride In the same manner as in Example 3, 15.55 g of (R)—(–)-5-amino-2,4,6,7-tetramethyl-2-(4 -phenylpiperidinomethyl)-2,3-dihydrobenzo[b]furan dihydrochloride was obtained from 20.03 g of (R)—(–)-5-amino-2,4,6,7-tetramethyl-2-(4 -phenylpiperidinomethyl)-2,3-dihydrobenzo[b]furan (R)—(–)—mandelate.

Melting point: 226° C. (decomposed)

$[\alpha]^{26}$:–27.9° (c=1.284, methanol)

Elemental analysis (for $C_{24}H_{32}N_2O \cdot H_2Cl_2$):

Calculated: C, 65.90; H, 7:83; N, 6.40; Cl, 16.21

Found: C, 65.76; H, 7.95; N, 6.31; Cl 16.04

Example 5

(S)—(+)-5-amino-2,4,6,7-tetramethyl-2-(4-phenylpiperidinomethyl)-2,3-dihydrobenzo [b]furan dimethanesulfonate 800 mg of (S)—(+)-5-ammino-2,4,6,7-tetramethyl-2-(4-phenylpiperidino-methyl) -2,3-dihydrobenzo[b]furan dihydrochloride was dispensed to ethyl acetate (10 ml) and a 0.5 N aqueous solution of sodium hydroxide (10 ml). The organic layer was washed by sequential additions of a saturated aqueous solution of sodium hydrogen carbonate and saturated saline and then dried over anhydrous sodium carbonate, followed by concentration to dryness. The resulting residue and 351 mg of methanesulfonic acid were dissolved in methanol, followed by concentration to dryness. To the resulting crystalline residue was added ethyl acetate; the resulting precipitate was collected by filtration and washed with ethyl acetate, to yield 950 mg of crystal of (S)—(+)— 5-amino-2,4,6,7-tetramethyi-2-(4-phenylpiperidinomethyl)-2,3-dihydrobenzo [b]furan dimethanesulfonate.

Melting point: 202°–211° C.

$[\alpha]^{25}$:+21.4° (c=1.340, methanol)

Elemental analysis (for $C_{24}H_{32}N_2O \cdot C_2H_8S_2O_6$):

Calculated: C, 56.09; H, 7.24; N, 5.03; S, 11.52

Found: C, 55.91; H, 7.25; N, 4.95; S, 11.23

Example 6

(S)—(+)-5-amino-2,4,6,7-tetramethyl-2-(4-phenylpiperidinomethyl)-2,3-dihydrobenzo [b]furan fumarate In the same manner as in Example 5, 543 mg of (S)—(+) -5-amino-2,4,6,7-tetramethyl-2-(4 -phenylpiperidinomethyl)-2,3-dihydrobenzo[b]furan fumarate was obtained from 800 mg of (S)—(+)-5-amino-2,4,6,7-tetramethyl-2-(4-phenylpipidinomethyl) -2,3-dihydrobenzo[b]furan dihydrochloride and 212 mg of fumaric acid.

Melting point: 177°–180° C. $[\alpha]^{25}$:+32.2 (c=1.070, methanol)

Elemental analysis (for $C_{24}H_{32}N_2O \cdot C_4H_4O_4$):

Calculated: C, 69.98; H, 7.55; N, 5.83

Found : C, 69.97; H, 7.54; N, 6.07

Example 7

(R)—(–)-5-amino-2,4,6,7-tetramethyl-2-(4-phenylpiperidinomethyl)-2,3-dihydrobenzo [b]furan dihydrobromide (R)—(–)-5-amino-2,4,6,7-tetramethyl-2-(4-phenylpiperidinomethyl )-2,3-dihydrobenzo [b]furan (860 mg) was dissolved in methanol and to the solution was added 25% hydrobromide in acetic acid solution (0.5 ml) and then concentrated. The residue was dissolved in methanol and left. The resulting crystal was collected by filtration and washed with ethanol to yield 810 mg of (R)—(–)-5-amino-2,4,6,7-tetramethyl-2-(4-phenylpiperidino-methyl)-2,3-dihydrobenzo [b]furan dihydrobromide.

Melting point: 220.5° C. (decomposed)

$[\alpha]^{20}_D$:+23.6 (c=0.86%, methanol)

Elemental analysis (for $C_{24}H_{32}N_2O \cdot 2HBr$):

Calculated: C, 54.77; H, 6.51; N, 5.32

Found: C, 54.47; H, 6.60; N, 5.17

Example 8

(R)—(–)-5-amino-2,4,6,7-tetramethyl-2-(4-phenylpiperidinomethyl)-2,3-dihydrobenzo [b]furan L-tartarate (R)—(–)-5-amino-2,4,6,7-tetramethyl-2-(4-phenylpiperidinomethyl )-2,3-dihydrobenzo [b]furan (870 mg) and L-tartaric acid (354 mg) were dissolved in methanol and then concentrated. The residue was dissolved in ethanol and left. The resulting crystal was collected by filtration and washed with ethanol to yield 970 mg of (R)—(–)-5-amino-2,4,6,7-tetramethyl-2-(4-phenylpiperidinomethyl) -2,3-dihydrobenzo[b]furan L-tartarate monoethanol.

Melting point: 130.5° C.

$[\alpha]^{20}_D$:+35.0 (c=0.755%, methanol)

Elemental analysis (for $C_{24}H_{32}N_2O_6 \cdot C_4H_6O_6 \cdot C_2H_5OH$):

Calculated: C, 64.26; H, 7.90; N, 5.00

Found : C, 64.32; H, 8.11; N, 4.92

Analytical Example 1

The compound of Example 67 of EP-A-0483772 and the compound of Example 1 were analyzed by high performance liquid chromatography, using an optical resolution column.

Operating conditions:

Column: Chiral Cell OD (4.6×250 mm)

Mobile phase: n-hexane-ethanol-diethylamine (100:0.5:0.1, v/v)

Flow rate: 1 1 ml/min

Detection: UV 254 nm

Figure 2:
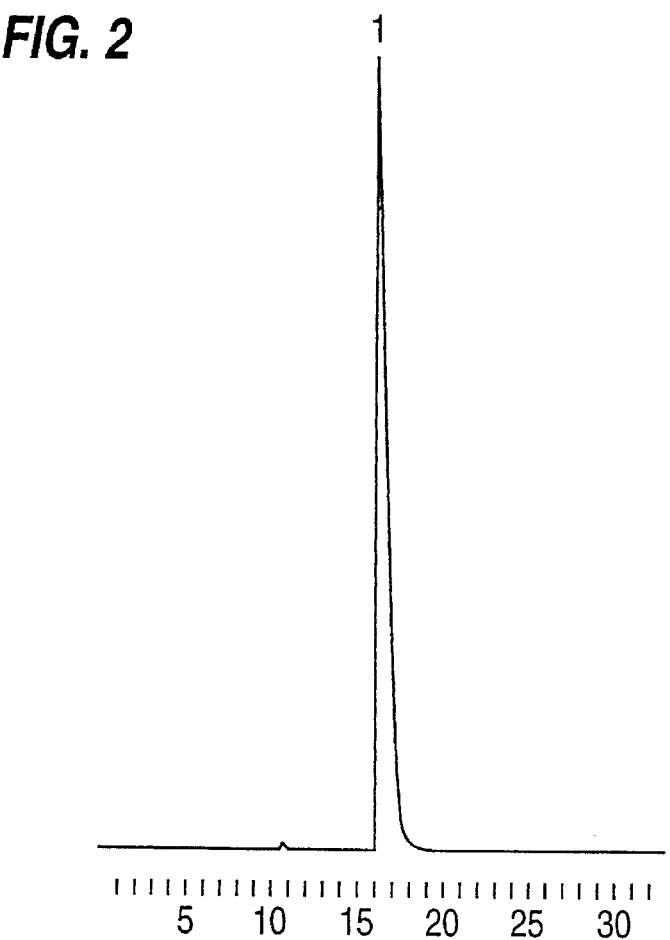
FIG. 2 shows the liquid chromatography results of the compound of Example 1 of the application.

The analytical results are given in FIG. 1 (the compound of Example 67 of EP-A-0483772) and FIG. 2 (the compound of Example 1).

The abscissa indicates retention time (min). Peaks 1 and 2 correspond to the (S)—(+) and (R)—(–) configurations, respectively.

Analytical Example 2

Figure 3:
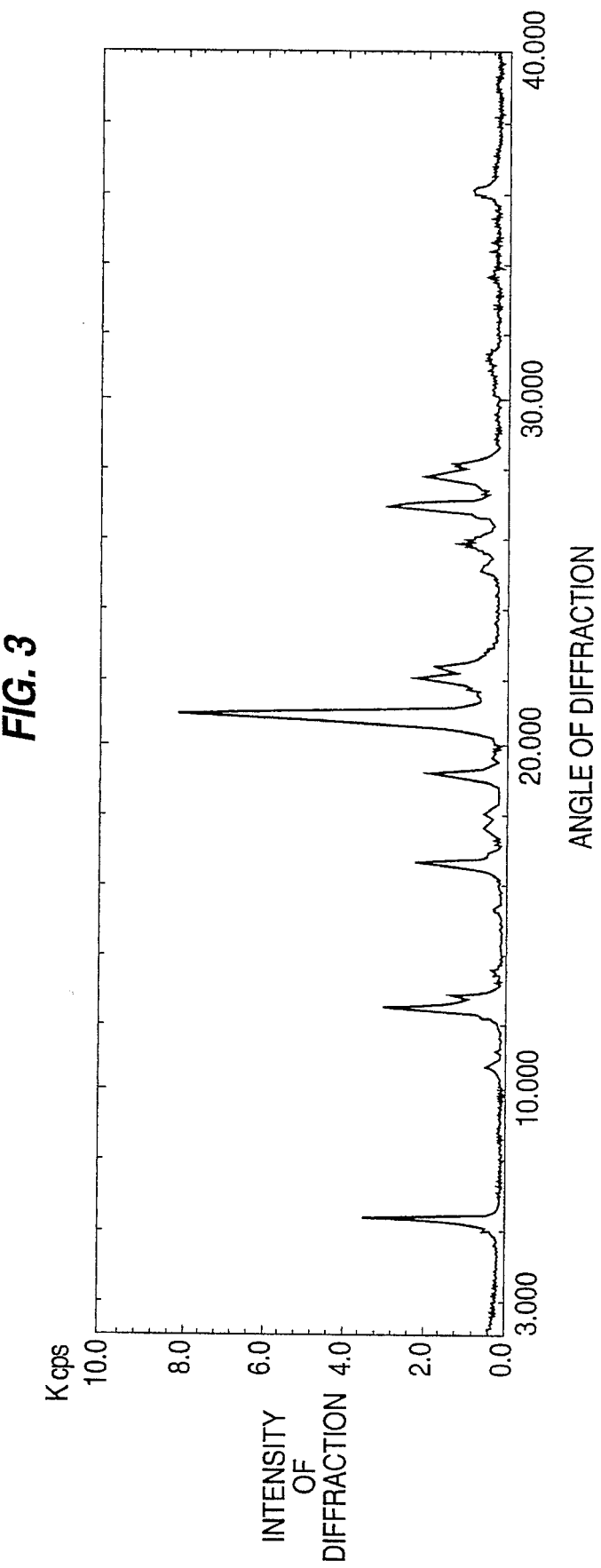
FIG. 3 shows the x-ray diffraction pattern of the compound of Example 3 of the application.

The powder X-ray diffraction pattern (CuKα, 40kV, 40mA) of the compound of Example 3 is shown in FIG. 3 (showing characteristic peaks at lattice spacings (d) of 13.89, 7.12, 5.36, 4.26, 4.05, 4.00, 3.31, 3.21).

Experiment 1

Effect on drugs on the change of behavior induced by spinal in intrathecal injection of $FeCl_2$ in mice.

Male SIc: IcR mice (5 weeks) (10 mice per group) were used. After injection of 5 μl/mouse physiological saline, containing 50 mM dissolved ferrous chloride, to the subarachnoid cavity from lumbar spinal cord VI to sacral spinal cord I, each animal was observed for behavioral changes from 15 minutes to 1 hour following injection. The following criteria were used to score behavioral changes.

Score Behavioral change

0: Normal

1: Frequent bites to lower limbs and lower abdomen.

2: One of the following three responses is seen:
   a) Violent bites to lower half of body, with occasionally rolling
   b) Hypersensitive aggressive behavior in response to external stimulation
   c) Tremors 3: Clonic convulsion 4: Tonic convulsion, or unilateral or bilateral limb paralysis 5: Death Percent inhibitions were calculated from the scores obtained as above (percent inhibition=[(5-score)/5]×100). The subject compound salt was orally administered during the 30-minute period following administration of ferrous chloride. Table i shows the mean scores and percent inhibitions obtained after a 25 mg/kg oral administration of each compound of Examples 3 and 4.

TABLE 1

|  | Mean Score | | |
| --- | --- | --- | --- |
|  | 25 mg/kg Administered | Physiological Saline Administered | Percent Suppression (%) |
| Example 3 | 0.2 | 5.0 | 96 |
| Example 4 | 1.3 | 4.7 | 72.3 |

These results demonstrate that the crystalline salts of the present invention are excellent in suppressing action against central nervous disorder associated with lipidperoxide formation by ferrous chloride.

The present invention provides a lipidperoxide formation inhibitor, particularly a crystalline salt of an enantiomer of 5-amino-2,4,6,7-tetramethyl-2-(4-phenylpiperidinomethyl)-2,3-dihydrobenzo[b]furan which serves well to improve, treat and prevent cerebral dysfunction associated with cerebral stroke or cranial trauma. The crystalline salt of the present invention is more soluble in water and more stable than the free form of the compound.

What we claimed is:

1. In the compound 5-amino-2,4,6,7-tetramethyl -2-(4-phenylpiperidinomethyl) -2,3-dihydrobenzo[b]furan or a salt thereof, the improvement which comprises providing said compound in the form of (S)—(+)-5-amino-2,4,6,7-tetramethyl-2- (4-phenylpiperidinomethyl)-2,3-dihydrobenzo[b] furan or a salt thereof in its crystalline state showing its characteristic peaks at lattice spacings (d) of 13.89, 7.12, 5.36, 4.26, 4.05, 4.00, 3.31, 3.21 in the powder of x-ray diffraction pattern.

2. The compound of claim 1 in the form of its hydrochloride.

3. (S)—(+)-5-amino-2,4,6,7-tetramethyl-2-(4-phenylpiperidinomethyl) -2,3-dihydrobenzo furan dihydrochloride showing is characteristic peaks at lattice spacings (d) of 13.89, 7.12, 5.36, 4.26, 4.05, 4.00, 3.31, 3.21, in the powder x-ray diffraction pattern.

\* \* \* \* \*

UNITED STATES PATENT AND TRADEMARK OFFICE
CERTIFICATE OF CORRECTION

PATENT NO. : 5,552,552  
DATED : September 3, 1996  
INVENTOR(S) : Shigenori OHKAWA et al.

Page 1 of 8

It is certified that error appears in the above-indentified patent and that said Letters Patent is hereby corrected as shown below:

On the title page, item [56], column 2:

"2054619 5/1992 European Pat. Off." should read --2054619 5/1992 Canada--.

In column 1, line 50, "a-position" should read --α-position--;

line 55, "eridonomethyl)" should read --eridinomethyl)--.

In column 3, line 36, "add" should read --acid--;

line 45, "butanol," should read --butanol),--;

UNITED STATES PATENT AND TRADEMARK OFFICE
CERTIFICATE OF CORRECTION

PATENT NO. : 5,552,552
DATED : September 3, 1996
INVENTOR(S) : Shigenori OHKAWA et al.

It is certified that error appears in the above-indentified patent and that said Letters Patent is hereby corrected as shown below:

line 55, "mount" should read --amount--;

line 62, "diastreomeric" should read --diastereomeric--.

In column 4, line 15, "mount" should read --amount--;

line 65, "eicosapentaenic" should read --eicosapentaenoic--.

In column 5, line 2, "5-hydroperoxyeicosatetraenic" should read --5-hydroperoxyeicosatetraenoic--;

line 3, "5-hydroxyeicosatetraenic" should read --5-hydroxyeicosatetraenoic";

line 23, "nervous" should read --nerve--;

lines 40 and 41, "arachi-donic" should read --arachidonate--;

UNITED STATES PATENT AND TRADEMARK OFFICE
CERTIFICATE OF CORRECTION

PATENT NO. : 5,552,552  
DATED : September 3, 1996  
INVENTOR(S) : Shigenori OHKAWA et al.

It is certified that error appears in the above-indentified patent and that said Letters Patent is hereby corrected as shown below:

line 67, "-2,3 -" should read -- -2,3- --.

In column 6, line 14, "(4 -phenylpiperidinom-" should read --(4-phenylpiperidinom- --;

line 17, "[$\alpha^{27}$:" should read --[$\alpha$]$_D^{27}$:--;

line 25, "dihydrobenzo [b]furan" should read --dihydrobenzo[b]furan--;

line 38, "drobenzo [b]furan" should read --drobenzo[b]furan--;

line 40, "[$\alpha$]$^{27}$:" should read --[$\alpha$]$_D^{27}$:--;

UNITED STATES PATENT AND TRADEMARK OFFICE
CERTIFICATE OF CORRECTION

PATENT NO. : 5,552,552
DATED : September 3, 1996
INVENTOR(S) : Shigenori OHKAWA et al.

It is certified that error appears in the above-indentified patent and that said Letters Patent is hereby corrected as shown below:

line 50, "nylpiperidino-methyl" should read --nylpiperidinomethyl--; "dihydrobenzo [b]furan" should read --dihydrobenzo[b]furan--;

line 64, "dihydrobenzo   [b]furan" should read --dihydrobenzo[b]furan--;

line 67, "$[\alpha]^{26}:+27.820$" should read --$[\alpha]_D^{26}:+27.8°$--.

In column 7, line 8, "dihydrobenzo   [b]furan" should read --dihydrobenzo[b]furan--;

line 10, "(4 - phenylpiperidinom-" should read --(4-phenylpiperidinom- --;

line 13, "(4-phenylpiperidinomethyl)" should read --(4-phenylpiperidinomethyl--;

line 16, "$[\alpha]^{26}:$" should read --$[\alpha]_D^{26}:$--;

UNITED STATES PATENT AND TRADEMARK OFFICE
CERTIFICATE OF CORRECTION

PATENT NO. : 5,552,552
DATED : September 3, 1996
INVENTOR(S) : Shigenori OHKAWA et al.

It is certified that error appears in the above-indentified patent and that said Letters Patent is hereby corrected as shown below:

line 24, "dihydrobenzo [b]furan" should read --dihydrobenzo[b]furan--;

line 26, "phenylpiperidino-methyl" should read --phenylpiperidinomethyl--;

line 38, "tetramethyi" should read --tetramethyl--;

lines 39 and 50, "dihydrobenzo [b]furan" should read --dihydrobenzo[b]furan--;

line 42, "$[\alpha]^{25}$:" should read --$[\alpha]_D^{25}$:--;

line 52, "(4 -phenylpiperidinom-" should read --(4-phenylpiperidinom- --;

line 55, ") -2,3-" should read --)-2,3- --;

line 57, "$[\alpha]^{25}$:+32.2" should read --$[\alpha]_D^{25}$:+32.2°--;

line 67, "dihydrobenzo [b]furan" should read --dihydrobenzo[b]furan--.

UNITED STATES PATENT AND TRADEMARK OFFICE
CERTIFICATE OF CORRECTION

PATENT NO. : 5,552,552
DATED : September 3, 1996
INVENTOR(S) : Shigenori OHKAWA et al.

It is certified that error appears in the above-indentified patent and that said Letters Patent is hereby corrected as shown below:

In column 8, line 2, "dihydrobenzo [b]furan" should read --dihydrobenzo[b]furan--;

line 8, "phenylpiperidiono-methyl" should read --phenylpiperidinomethyl--;

lines 8, 9, 19 and 21, "dihydrobenzo [b]furan" should read --dihydrobenzo[b]furan--;

line 11, "$[\alpha]^{20}_D$:+23.6 (c=0.86%," should read --$[\alpha]^{20}_D$:+23.6° (c=0.86,--;

line 26, ") -2,3-" should read --)-2,3- --;

line 29, "$[\alpha]^{20}_D$:+35.0 (c=0.755%," should read --$[\alpha]^{20}_D$:+35.0° (c=0.755,--;

line 44, "1 1 ml/min" should read --1 ml/min--.

In column 9, line 21, "Table i" should read --Table 1--.

UNITED STATES PATENT AND TRADEMARK OFFICE
CERTIFICATE OF CORRECTION

PATENT NO. : 5,552,552
DATED : September 3, 1996
INVENTOR(S) : Shigenori OHKAWA et al.

It is certified that error appears in the above-indentified patent and that said Letters Patent is hereby corrected as shown below:

In column 10, line 13, "claimed" should read --claim--;

line 14, claim 1, "tetramethyl -2-" should read --tetramethyl-2 --;

line 15, claim 1, ") -2,3-" should read --)-2,3- --;

line 18, claim 1, "-2- (4-" should read -- -2-(4- --;

line 19, claim 1, "drobenzol[b] furan" should read --drobenzo[b]furan--;

line 22, claim 1, delete "of";

line 26, claim 3, ") -2,3-dihydrobenzo furan" should read --)-2,3-dihydrobenzo[b]furan--;

UNITED STATES PATENT AND TRADEMARK OFFICE
CERTIFICATE OF CORRECTION

PATENT NO. : 5,552,552
DATED : September 3, 1996
INVENTOR(S) : Shigenori OHKAWA et al.

It is certified that error appears in the above-indentified patent and that said Letters Patent is hereby corrected as shown below:

line 27, claim 3, "is" should read --its--.

Signed and Sealed this

Twelfth Day of August, 1997

Attest:

BRUCE LEHMAN

Attesting Officer

Commissioner of Patents and Trademarks